United States Patent
Wang et al.

(10) Patent No.: US 12,106,473 B2
(45) Date of Patent: *Oct. 1, 2024

(54) MEDICAL IMAGE ANALYZING SYSTEM FOR IDENTIFYING PANCREATIC CANCER USING MACHINE LEARNING AND METHOD THEREOF

(71) Applicant: National Taiwan University, Taipei (TW)

(72) Inventors: Wei-Chung Wang, Taipei (TW); Wei-Chih Liao, Taipei (TW); Kao-Lang Liu, Taipei (TW); Po-Ting Chen, Taipei (TW); Po-Chuan Wang, Taipei (TW); Da-Wei Chang, Taipei (TW)

(73) Assignee: National Taiwan University, Taipei (TW)

( * ) Notice: Subject to any disclaimer, the term of this patent is extended or adjusted under 35 U.S.C. 154(b) by 447 days.

This patent is subject to a terminal disclaimer.

(21) Appl. No.: 17/507,949

(22) Filed: Oct. 22, 2021

(65) Prior Publication Data

US 2022/0156929 A1    May 19, 2022

Related U.S. Application Data

(60) Provisional application No. 63/104,568, filed on Oct. 23, 2020.

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/425* (2013.01); *A61B 5/4887* (2013.01); *A61B 5/726* (2013.01);
(Continued)

(58) Field of Classification Search
CPC .......... G06T 7/0012; G06T 7/73; G06T 7/70; G06T 2207/20016; G06T 2207/20064;
(Continued)

(56) References Cited

U.S. PATENT DOCUMENTS 10,803,987 B2 * 10/2020 Bériault ................. G06N 3/045
11,583,698 B2 *  2/2023 Yin ......................... A61N 5/103

OTHER PUBLICATIONS

P. Wang, Automated Pancreas Segmentation Using Multi-institutional Collaborative Deep Learning, Sep. 2020 (Year: 2020).*

(Continued)

*Primary Examiner* — Stephen S Hong
*Assistant Examiner* — Carl E Barnes, Jr.
(74) *Attorney, Agent, or Firm* — Amin, Turocy & Watson, LLP (57) ABSTRACT

A medical image analyzing system and a medical image analyzing method are provided and include inputting at least one patient image into a first model of a neural network module to obtain a result having determined positions and ranges of an organ and a tumor of the patient image; inputting the result into a second model of a first analysis module and a third model of a second analysis module, respectively, to obtain at least one first prediction value and at least one second prediction value corresponding to the patient image; and outputting a determined result based on the first prediction value and the second prediction value. Further, processes between the first model, the second model and the third model can be automated, thereby improving identification rate of pancreatic cancer.

28 Claims, 2 Drawing Sheets

(51) Int. Cl.
*G06N 3/08* (2023.01)
*G06T 7/70* (2017.01)
*G06T 7/73* (2017.01)
*G06V 10/774* (2022.01)
*G06V 10/776* (2022.01)
*G06V 10/82* (2022.01)
*G16H 30/20* (2018.01)

(52) U.S. Cl.
CPC .............. *A61B 5/7267* (2013.01); *G06N 3/08* (2013.01); *G06T 7/70* (2017.01); *G06T 7/73* (2017.01); *G06V 10/774* (2022.01); *G06V 10/776* (2022.01); *G06V 10/82* (2022.01); *G16H 30/20* (2018.01); *G06T 2207/20016* (2013.01); *G06T 2207/20064* (2013.01); *G06T 2207/20081* (2013.01); *G06T 2207/20084* (2013.01); *G06T 2207/30096* (2013.01); *G06T 2207/30204* (2013.01); *G06V 2201/031* (2022.01)

(58) Field of Classification Search
CPC . G06T 2207/20081; G06T 2207/20084; G06T 2207/30096; G06T 2207/30204; G16H 30/20; G06V 10/82; G06V 10/774; G06V 10/776; G06V 2201/031; A61B 5/425; A61B 5/4887; A61B 5/726; A61B 5/7267; G06N 3/08
See application file for complete search history.

(56) References Cited

OTHER PUBLICATIONS

Ying Liang, Auto-segmentation of pancreatic tumor in multi-parametric MRI using deep convolutional neural networks, Feb. 8, 2020 (Year: 2020).*
Qihang Yu, C2FNAS: Coarse-to-Fine Neural Architecture Search for 3D Medical Image Segmentation, Apr. 2020 (Year: 2020).*
Po-Ting, Chen Pancreatic Cancer Detection on CT Scans with Deep Learning, 2023 (Year: 2023).*
Meng-meng Wang Comparison and screening of different risk assessment models for deep vein thrombosis in patients with solid tumors, May 2019 (Year: 2019).*
Kaushik Sekaran, Deep learning convolutional neural network (CNN) With Gaussian mixture model for predicting pancreatic cancer, 2019 (Year: 2019).*
Jingjing Yin, Joint confidence region estimation for area under ROC curve and Youden index, 2013 (Year: 2013).*
Sehmi, M., Pancreatic cancer grading in pathological images using deep learning CNN (Year: 2021).*
Hiroshi, Miyamoto, Tumor Volume Index as a Prognostic Factor in Patients after Curative Esophageal Cancer Resection (Year: 2019).*

* cited by examiner

MEDICAL IMAGE ANALYZING SYSTEM FOR IDENTIFYING PANCREATIC CANCER USING MACHINE LEARNING AND METHOD THEREOF

BACKGROUND

1. Technical Field

The present disclosure relates to image analyzing system and method, and more particularly, to medical image analyzing system and method.

2. Description of Related Art

In the current medical practice, pancreatic cancer is one of the cancers that are difficult to detect early, and the survival rate of pancreatic cancer decreases significantly once the tumor size exceeds 2 cm. In the prior art, computerized tomography (CT) imaging is currently the main method for detecting and evaluating pancreatic cancer, but the detection efficiency still depends on the personal experience of radiologists. For example, when the tumor size is less than 2 cm, about 40% of the tumor cannot be detected, which reflects the fact that manual review and diagnosis are too subjective, and it is easy to misdiagnose due to human factors.

Therefore, there is a need in the art to propose a medical image analyzing system and a medical image analyzing method for identifying pancreatic cancer and improving the identification rate of pancreatic cancer.

SUMMARY

In view of the aforementioned problems of the prior art, the present disclosure provides a medical image analyzing system, which comprises a neural network module having a first model and configured to input at least one patient image into the first model to obtain a result of determined positions and ranges of an organ and a tumor of the patient image; a first analysis module having a second model and configured to input the result of the determined positions and ranges of the organ and the tumor of the patient image into the second model to obtain at least one first prediction value corresponding to the patient image; a second analysis module having a third model and configured to input the result of the determined positions and ranges of the organ and the tumor of the patient image into the third model to obtain at least one second prediction value corresponding to the patient image; and a determining module configured to output a determined result based on the first prediction value and the second prediction value.

In the aforementioned medical image analyzing system, the present disclosure further comprises a database stored with a plurality of images, organ position and range markers and tumor position and range markers, wherein the plurality of images, the organ position and range markers and the tumor position and range markers are interlinked to use as a first training set.

In the aforementioned medical image analyzing system, the neural network module is trained to obtain the first model based on the first training set, wherein the neural network module is a model searched by using a coarse-to-fine neural structure search (C2FNAS), and wherein the neural network module uses an Adam optimizer and a cosine annealing learning rate scheduler to adjust a learning rate in a range of $10^{-3}$ to $10^{-5}$, and a loss function is set to a Dice loss combined with a categorical cross-entropy loss.

In the aforementioned medical image analyzing system, the neural network module obtains a result having determined positions and ranges of the organ and the tumor of the plurality of images by inputting the plurality of images into the first model and uses the result as a second training set.

In the aforementioned medical image analyzing system, the first analysis module first performs 3D feature analysis on the second training set using an algorithm of radiomics to obtain a plurality of 3D feature values, and then trains a machine learning algorithm of a gradient boosting decision tree using the plurality of 3D feature values to obtain the second model.

In the aforementioned medical image analyzing system, the first analysis module uses a plurality of filters to extract 3D features, wherein the plurality of filters include 3 Laplacian of Gaussian filters, 8 wavelet transformation filters and 1 gradient filter.

In the aforementioned medical image analyzing system, the second analysis module first performs 2D feature analysis on the second training set using the algorithm of radiomics to obtain a plurality of 2D feature values, and then trains a machine learning algorithm of a gradient boosting decision tree using the plurality of 2D feature values to obtain the third model.

In the aforementioned medical image analyzing system, the second analysis module uses a plurality of filters to extract 2D features, wherein the plurality of filters include 4 wavelet transformation filters and 1 gradient filter.

In the aforementioned medical image analyzing system, features selected by the radiomics include first order features, gray level co-occurrence matrix features, gray level dependence matrix features, gray level run length matrix features, gray level size zone matrix features, or neighboring gray tone difference matrix features.

In the aforementioned medical image analyzing system, the present disclosure further comprises a threshold-value selection module configured to plot a curve for the first prediction value or the second prediction value, wherein a threshold value for determining whether there is cancer is determined from the curve, such that the first analysis module or the second analysis module determines whether the first prediction value or the second prediction value represents having cancer based on the threshold value.

In the aforementioned medical image analyzing system, the curve is a receiver operating characteristic curve, and the threshold value is a corresponding threshold value corresponding to a maximum value of a Youden index.

In the aforementioned medical image analyzing system, the Youden index is calculated from a sensitivity and a specificity corresponding to each point in the curve according to a formula Youden index=sensitivity+specificity−1.

In the aforementioned medical image analyzing system, the determining module uses an outcome probability of a logistic regression model as the determined result, wherein the logistic regression model is obtained based on the first prediction value and the second prediction value.

In the aforementioned medical image analyzing system, the determining module uses one or both of the first prediction value and the second prediction value representing having cancer as the determined result.

In the aforementioned medical image analyzing system, the present disclosure further comprises an image preprocessing module configured to process the patient image by resampling, windowing and normalization before inputting into the first model, the second model, or the third model.

The present disclosure further provides a medical image analyzing method, which comprises the steps of: obtaining at least one patient image; inputting the patient image into a first model of a neural network module to obtain a result having determined positions and ranges of an organ and a tumor of the patient image; inputting the result having determined positions and ranges of the organ and the tumor of the patient image into a second model of a first analysis module and a third model of a second analysis module, respectively, to obtain at least one first prediction value corresponding to the patient image and at least one second prediction value corresponding to the patient image; and outputting a determined result by a determining module according to the first prediction value and the second prediction value.

In the aforementioned medical image analyzing method, the present disclosure further comprises the step of: interlinking a plurality of images, organ position and range markers and tumor position and range markers to use as a first training set via a database stored with the plurality of images, the organ position and range markers and the tumor position and range markers.

In the aforementioned medical image analyzing method, the neural network module is trained to obtain the first model based on the first training set, wherein the neural network module is a model searched by using a coarse-to-fine neural structure search (C2FNAS), and wherein the neural network module uses an Adam optimizer and a cosine annealing learning rate scheduler to adjust a learning rate in a range of $10^{-3}$ to $10^{-5}$, and a loss function is set to a Dice loss combined with a categorical cross-entropy loss.

In the aforementioned medical image analyzing method, the neural network module obtains a result having determined positions and ranges of the organ and the tumor of the plurality of images by inputting the plurality of images into the first model and uses the result as a second training set.

In the aforementioned medical image analyzing method, the first analysis module first performs 3D feature analysis on the second training set using an algorithm of radiomics to obtain a plurality of 3D feature values, and then trains a machine learning algorithm of a gradient boosting decision tree using the plurality of 3D feature values to obtain the second model.

In the aforementioned medical image analyzing method, the first analysis module uses a plurality of filters to extract 3D features, wherein the plurality of filters include 3 Laplacian of Gaussian filters, 8 wavelet transformation filters and 1 gradient filter.

In the aforementioned medical image analyzing method, the second analysis module first performs 2D feature analysis on the second training set using the algorithm of radiomics to obtain a plurality of 2D feature values, and then trains a machine learning algorithm of a gradient boosting decision tree using the plurality of 2D feature values to obtain the third model.

In the aforementioned medical image analyzing method, the second analysis module uses a plurality of filters to extract 2D features, wherein the plurality of filters include 4 wavelet transformation filters and 1 gradient filter.

In the aforementioned medical image analyzing method, features selected by the radiomics include first order features, gray level co-occurrence matrix features, gray level dependence matrix features, gray level run length matrix features, gray level size zone matrix features, or neighboring gray tone difference matrix features.

In the aforementioned medical image analyzing method, the present disclosure further comprises the step of: plotting a curve for the first prediction value or the second prediction value by a threshold-value selection module, wherein a threshold value for determining whether there is cancer is determined from the curve, such that the first analysis module or the second analysis module determines whether the first prediction value or the second prediction value represents having cancer based on the threshold value.

In the aforementioned medical image analyzing method, the curve is a receiver operating characteristic curve, and the threshold value is a corresponding threshold value corresponding to a maximum value of a Youden index.

In the aforementioned medical image analyzing method, the Youden index is calculated from a sensitivity and a specificity corresponding to each point in the curve according to a formula Youden index=sensitivity+specificity−1.

In the aforementioned medical image analyzing method, the determining module uses an outcome probability of a logistic regression model as the determined result, wherein the logistic regression model is obtained based on the first prediction value and the second prediction value.

In the aforementioned medical image analyzing method, the determining module uses one or both of the first prediction value and the second prediction value representing having cancer as the determined result.

In the aforementioned medical image analyzing method, the present disclosure further comprises the step of: enabling an image preprocessing module to process the patient image by resampling, windowing and normalization before inputting into the first model, the second model, or the third model.

In conclusion, the medical image analyzing system and method according to the present disclosure have higher sensitivity than radiologists in identifying pancreatic cancer, which means that the medical image analyzing system and method according to the present disclosure can effectively assist radiologists in reducing their clinical missed diagnosis rate, especially in the case of tumors less than 2 cm in size. Therefore, the situation that about 40% of the tumors cannot be detected when the tumor is less than 2 cm in size can be effectively improved. In addition, the medical image analyzing system and method according to the present disclosure are automated processes. After directly inputting the original medical image, the medical image analyzing system and method according to the present disclosure can automatically identify the potential positions and ranges of pancreas and tumor and automatically determine and classify whether the original medical image contains pancreatic cancer.

DETAILED DESCRIPTION OF THE EMBODIMENTS

The following illustrative embodiments are provided to illustrate the present disclosure, these and other advantages and effects can be apparent to those in the art after reading this specification.

Figure 1:
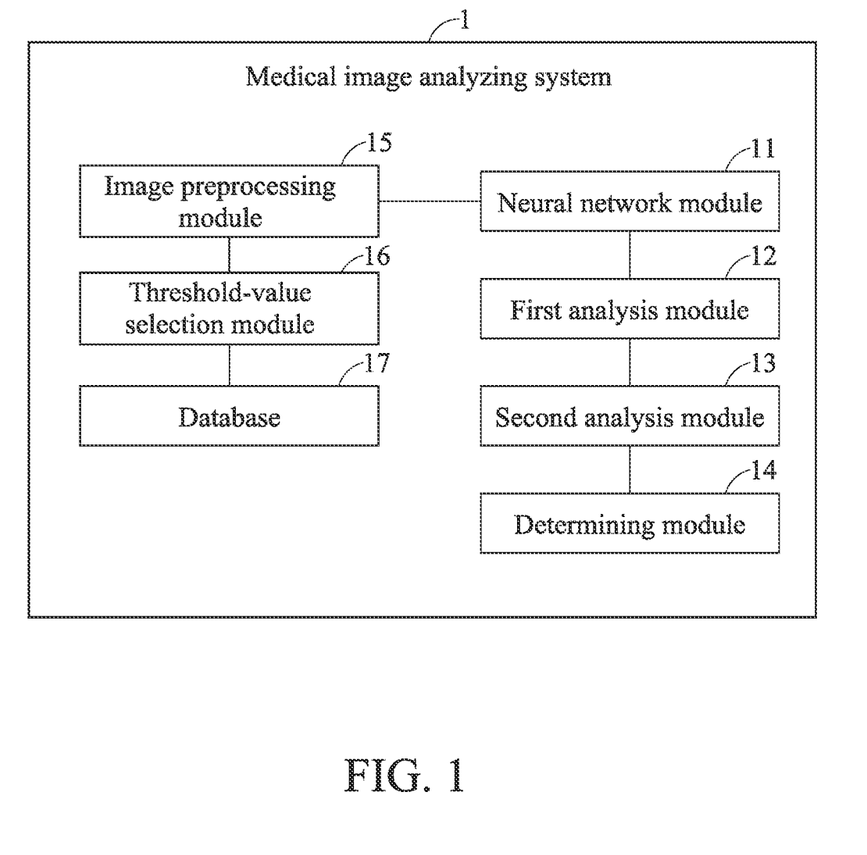
FIG. 1 is a system architecture diagram of a medical image analyzing system according to the present disclosure.

Referring to FIG. 1, a medical image analyzing system 1 according to the present disclosure includes a neural network module 11, a first analysis module 12, a second analysis module 13, a determining module 14, an image preprocessing module 15, a threshold-value selection module 16 and a database 17. The medical image analyzing system 1 according to the present disclosure can operate on devices such as mobile phones, tablet computers, laptops, desktop computers, servers, or cloud servers. The neural network module 11, the first analysis module 12, the second analysis module 13, the determining module 14, the image preprocessing module 15 and the threshold-value selection module 16 can respectively be code fragments, software, or firmware stored in the database 17 or a storage unit, and can be executed by a processing unit, and can also be implemented by other hardware or combinations of software and hardware. The processing unit can be a central processing unit (CPU), a microprocessor, a graphics processing unit (GPU), or an application specific integrated circuit (ASIC). The storage unit can be a combination of any type of fixed or removable random-access memory (RAM), read-only memory (ROM), flash memory, hard disk, soft disk, database, or similar elements. However, the present disclosure is not limited thereto.

In an embodiment, the neural network module 11 has a first model. After inputting at least one patient image into the first model, a result having determined positions and ranges of an organ and a tumor of the patient image can be obtained. The first analysis module 12 has a second model. After inputting the result having determined positions and ranges of the organ and the tumor of the patient image into the second model, at least one first prediction value corresponding to the patient image can be obtained. The second analysis module 13 has a third model. After inputting the result having determined positions and ranges of the organ and the tumor of the patient image into the third model, at least one second prediction value corresponding to the patient image can be obtained. In an embodiment, the patient image can be a two-dimensional (2D) CT image or a three-dimensional (3D) CT image, and the present disclosure is not limited as such. The first model is a model trained by a neural network. The second model and the third model are models obtained by an algorithm of radiomics and a machine learning algorithm of a gradient boosting decision tree. The training stages of the first model, the second model and the third model are described below.

The database 17 can store a plurality of images, organ position and range markers, and tumor position and range markers, and the plurality of images, organ position and range markers, and tumor position and range markers are interlinked (e.g., linked to each other). The interlink referred herein is to plot the organ position and range markers, the tumor position and range markers, or both on the image at the same time, and the organ can be a pancreas. In addition, the image can be a 2D CT image or a 3D CT image, the organ position and range markers can be a contour of the pancreas, the tumor position and range markers can be a contour of the tumor portion in the pancreas, and the organ position and range markers and the tumor position and range markers can be marked by an experienced radiologist according to actual diagnosis data. In an embodiment, all data of the plurality of interlinked images, organ position and range markers and tumor position and range markers are used as a first training set.

The neural network module 11 can be trained to obtain the first model based on the first training set. The neural network module 11 is a deep learning model architecture based on SegNet or U-Net, for instance, a model searched by NVIDIA using a coarse-to-fine neural structure search (C2FNAS). During a training process, the neural network module 11 can use Adam optimizer and cosine annealing learning rate scheduler to adjust a learning rate in a range of $10^{-3}$ to $10^{-5}$, and a loss function is set to a Dice loss combined with a categorical cross-entropy loss.

In an embodiment, the deep learning model architecture based on SegNet or U-Net can be as follows. In a first level, an image of 96×96×96 pixels is inputted; after feature extraction is performed by a stem 3×3×3 convolution layer, 32 feature images of 96×96×96 pixels are outputted; after feature extraction using the stem 3×3×3 convolution layer with a stride of 2, 64 feature images of 48×48×48 pixels are outputted; and then entering to a second level. In the second level, another 64 feature images of 48×48×48 pixels are obtained via a 2D 3×3×1 convolution layer with said 64 feature images of 48×48×48 pixels (feature 2-1); after using pseudo 3D (P3D) 3×3×1+1×1×3 convolution layers, the feature images are added with the feature 2-1 to obtain another 64 feature images of 48×48×48 pixels (feature 2-2); after feature extraction using a 3D 3×3×3 convolution layer with a stride of 2, 128 feature images of 24×24×24 pixels are outputted; and then entering to a third level. In the third level, after feature extraction using the 3D 3×3×3 convolution layer with said 128 feature images of 24×24×24 pixels, another 128 feature images of 24×24×24 pixels (feature 3-1) are obtained; after feature extraction using the 3D 3×3×3 convolution layer with a stride of 2, 256 feature images of 12×12×12 pixels are outputted; and then entering to a fourth level. In the fourth level, after feature extraction using the 2D 3×3×1 convolution layer with a stride of 2 with said 256 feature images of 12×12×12 pixels (feature 4-1), 512 feature images of 6×6×6 pixels are outputted; and then a process of feature decoding can be performed.

After the 512 images of 6×6×6 pixels are feature restored by trilinear upsample and added with another 256 feature images of 12×12×12 pixels (which are obtained after the feature 4-1 passes through the 3D 3×3×3 convolution layer), 256 feature images of 12×12×12 pixels are outputted. Said 256 feature images of 12×12×12 pixels pass through the 3D 3×3×3 convolution layer to generate another 256 feature images of 12×12×12 pixels. After said another 256 feature images of 12×12×12 pixels are feature restored by trilinear upsample and added with another 128 feature images of 24×24×24 pixels (which are obtained after the feature 3-1 passes through the P3D 3×3×1+1×1×3 convolution layers), 128 feature images of 24×24×24 pixels are outputted. After said 128 feature images of 24×24×24 pixels are feature restored by trilinear upsample and added with another 64 feature images of 48×48×48 pixels (which are obtained after the feature 2-2 passes through the 3D 3×3×3 convolution layer), 64 feature images of 48×48×48 pixels are outputted. Said 64 feature images of 48×48×48 pixels (feature 5-1) pass through the 2D 3×3×1 convolution layer and another 64 feature images of 48×48×48 pixels (feature 5-2) are obtained. After said another 64 feature images of 48×48×48 pixels pass through the 3D 3×3×3 convolution layer and add with the feature 5-1, another 64 feature images of 48×48×48 pixels are obtained. After said another 64 feature images of 48×48×48 pixels pass through the stem 3×3×3 convolution layer, another 64 feature images of 48×48×48 pixels are obtained. After said another 64 feature images of 48×48×48 pixels and the feature 5-2 are feature restored by trilinear upsample and added together, 32 feature images of 96×96×96 pixels are outputted. Finally, after performing feature decoding to said 32 feature images of 96×96×96 pixels via the stem 3×3×3 convolution layer, one feature image of 96×96×96 pixels is outputted. At this time, the size of the feature image of the last level is equal to the size of the image of the first level.

The neural network module 11 can input the plurality of images to the trained first model so as to obtain a result of determined positions and ranges of an organ and a tumor of the plurality of images and use the result as a second training set. The result can be a mask of the positions and ranges of the organ and the tumor, or the result can be an image of the positions and ranges of the organ and the tumor that have been marked, and the present disclosure is not limited as such. The first analysis module 12 can be trained to obtain the second model based on the second training set, and the second analysis module 13 can also be trained to obtain the third model based on the second training set.

The first analysis module 12 first performs a 3D feature analysis on the second training set by using an algorithm of radiomics to obtain a plurality of 3D feature values. The so-called radiomics can capture quantitative information about density, shape, or texture in the image, analyze radiomics feature via machine learning algorithms, and build classification/regression models via example learning so as to show patterns/rules that cannot be recognized by the naked eye in the image. The algorithm of radiomics can analyze many kinds of features. In an embodiment, the selected feature includes first order features, gray level co-occurrence matrix (GLCM) features, gray level dependence matrix (GLDM) features, gray level run length matrix (GLRLM) features, gray level size zone matrix (GLSZM) features, or neighboring gray tone difference matrix (NGTDM) features.

In an embodiment, the radiomics according to the present disclosure can select a total of 91 features (listed in Table 1) including 18 first order features, 22 gray level co-occurrence matrix features, 14 gray level dependence matrix features, 16 gray level run length matrix features, 16 gray level size zone matrix features and 5 neighboring gray tone difference matrix features to perform feature analysis, and a spacing or bin width for calculating texture features is fixed at 16.

TABLE 1

| | |
|---|---|
| First order feature | 10 percentile, 90 percentile, energy, entropy, interquartile range, kurtosis, maximum, mean, mean absolute deviation, median, minimum, range, robust mean absolute deviation, root mean squared, skewness, total energy, uniformity, variance. |
| Gray level co-occurrence matrix feature | autocorrelation, cluster prominence, cluster shade, cluster tendency, contrast, correlation, difference average, difference entropy, difference variance, ID, IDM, IDMN, IDN, IMC1, IMC2, inverse variance, joint average, joint energy, joint entropy, maximum probability, sum entropy, sum squares. |
| Gray level dependence matrix feature | dependence entropy, dependence non uniformity, dependence non uniformity normalized, dependence variance, gray level non uniformity, gray level variance, high gray level emphasis, large dependence emphasis, large dependence high gray level emphasis, large dependence low gray level emphasis, low gray level emphasis, small dependence emphasis, small dependence high gray level emphasis, small dependence low gray level emphasis. |
| Gray level run length matrix feature | gray level non uniformity, gray level non uniformity normalized, gray level variance, high gray level run emphasis, long run emphasis, long run high gray level emphasis, long run low gray level emphasis, low gray level run emphasis, run entropy, run length non uniformity, run length non uniformity normalized, run percentage, run variance, short run emphasis, short run high gray level emphasis, short run low gray level emphasis. |
| Gray level size zone matrix feature | gray level non uniformity, gray level non uniformity normalized, gray level variance, high gray level zone emphasis, large area emphasis, large area high gray level emphasis, large area low gray level emphasis, low gray level zone emphasis, size zone non uniformity, size zone non uniformity normalized, small area emphasis, small area high gray level emphasis, small area low gray level emphasis, zone entropy, zone percentage, zone variance. |
| Neighboring gray tone difference matrix feature | busyness, coarseness, complexity, contrast, strength. |

The first analysis module 12 can further first use a plurality of filters to extract 3D features. The plurality of filters include 3 Laplacian of Gaussian filters (parameter sigma is set to 1, 2 and 3), 8 wavelet transformation filters and 1 gradient filter. The wavelet transformation filter has high pass filter (H) and low pass filter (L) such as HHH, HHL, HLH, HLL, LHH, LHL, LLH and LLL. Therefore, the first analysis module 12 uses the filters and itself to extract a total of 1183 features (e.g., (12+1)×91=1183) for performing analysis (i.e., one image can have 1183 feature values).

After obtaining the plurality of 3D feature values, the first analysis module 12 can input the plurality of 3D feature values to a machine learning algorithm of a gradient boosting decision tree (XGboost) so as to train the machine learning algorithm and obtain the second model. The so-called machine learning algorithm of a gradient boosting decision tree can sequentially build a series of a plurality of decision trees to achieve classification purpose. For instance, in a method of building the plurality of decision trees, a decision tree is added after building a decision tree, so that the subsequent decision tree can improve the misclassification (e.g., classification error) of the previous decision tree. In this way, each decision tree can minimize the misclassification of the previous decision tree, and the second model is the classification predicted by all the decision trees. In an embodiment, a loss function of the machine learning algorithm of the gradient boosting decision tree can be set as logistic loss. After the image (or patient image) is inputted to the second model, the second model can output a first prediction value corresponding to the image (or patient image).

The second analysis module 13 also first performs a 2D feature analysis on the second training set via an algorithm of radiomics to obtain a plurality of 2D feature values. In an embodiment, the 91 features selected by the second analysis module 13 are the same as the first analysis module 12, and the machine learning algorithm of the gradient boosting decision tree used by the second analysis module 13 is also the same as the first analysis module 12 (as such, description thereof is omitted herein). In addition, the second analysis module 13 first uses a plurality of filters to extract 2D features, and the filters include 4 wavelet transformation filters and 1 gradient filter. The wavelet transformation filter has high pass filter (H) and low pass filter (L) such as HH, HL, LH and LL. Therefore, the second analysis module 13 uses the filters and itself to extract a total of 546 features (e.g., (5+1)×91=546) for performing analysis. Due to calculation, the IMC2 in the gray level co-occurrence matrix feature must be excluded in the gradient filter. As such, in the second analysis module 13, one image can have 545 feature values for performing 2D analysis. After obtaining the plurality of 2D feature values, the second analysis module 13 can input the plurality of 2D feature values to a machine learning algorithm of a gradient boosting decision tree so as to train the machine learning algorithm and obtain the third model. After the image (or patient image) is inputted to the third model, the third model can output a second prediction value corresponding to the image (or patient image).

The above described the training stages of the first model, the second model and the third model. In actual application stage, a program can be written to directly use the output of the first model as the input of the second model and the third model so as to achieve automation effect. For example, python can be used to write code, and PyRadiomics platform can be used to extract all the features of radiomics. Therefore, a user only needs to input one or a plurality of patient images to the first model, and the first model will output a result having determined positions and ranges of an organ and a tumor of the patient image. Said result can be automatically inputted to the second model and the third model so as to output the first prediction value and the second prediction value corresponding to the patient image, respectively.

Whether in the training stage or the application stage, the following method can be used to classify the first prediction value and the second prediction value. The threshold-value selection module 16 can determine a first threshold value to classify the first prediction value as having cancer or not having cancer, and can determine a second threshold value to classify the second prediction value as having cancer or not having cancer. The method for determining the first threshold value is the same as the method for determining the second threshold value. The prediction value and the threshold value are described below. For instance, after obtaining the plurality of prediction values, the threshold-value selection module 16 uses a specific threshold value to determine the plurality of prediction values so as to calculate statistical indicators (which include sensitivity and specificity, etc.) corresponding to the specific threshold value. Further, a plurality of sensitivities and specificities calculated according to possible values of the plurality of specific threshold values can be plotted as a curve, and the curve can be a receiver operating characteristic (ROC) curve. Then, from the receiver operating characteristic curve, statistical indicators such as area under receiver operating characteristic (AUC) curve and a plurality of Youden indexes, etc. can be obtained. The plurality of Youden indexes are calculated from the sensitivity and the specificity corresponding to each point in the curve according to the formula: Youden index=sensitivity+specificity−1. The threshold value corresponding to the maximum value in the plurality of Youden indexes according to the present disclosure is used as a threshold value. When the prediction value of the image (or patient image) is greater than the threshold value, the prediction value can be classified as having cancer (positive), otherwise it can be classified as not having cancer (negative).

The determining module 14 can output a determined result according to the first prediction value and the second prediction value. The determining module 14 can output the determined result of having cancer when one of the first prediction value and the second prediction value is classified as having cancer. The determining module 14 can also output the determined result of having cancer when both the first prediction value and the second prediction value are classified as having cancer. In an embodiment, the determining module 14 can use an outcome probability of a logistic regression model as the determined result, where the logistic regression model is obtained by using the first prediction value and the second prediction value as the model parameters. The method of the logistic regression model is described as follows. In the training stage, the same set of input image and mask is respectively inputted into the second model and the third model, and the obtained first prediction value and the second prediction value are used as a set of training data of the logistic regression model. Therefore, the logistic regression model is a model having 2 parameters and 1 intercept term; and by using and training multiple sets of training data, the values of parameters and intercept terms in the logistic regression can be obtained. In addition, the outcome probability of the logistic regression model can select a threshold value via the threshold-value selection module 16 so as to determine whether the outcome probability (or probability value) of the logistic regression model represents having cancer.

In an embodiment, whether in the training stage or in the application stage, the image preprocessing module 15 can be used to process the patient image or the image in the database 17 before inputting into the first model, the second model, or the third model. For example, before inputting the first model, a CT volume can first be converted to R-A-S+ direction, the image can be resampled to the same spacing (1 mm, 1 mm, 1 mm), and then the intensity can be clipped to −200 HU to 250 HU (Hounsfield unit). Finally, an intensity value can be normalized to [−1, 1]. For another example, before inputting the second model and the third module, all the images, the organ position and range markers and the tumor position and range markers can be resampled to the same spacing (1 mm, 1 mm, 5 mm) using a linear interpolation and a nearest-neighbor interpolation so as to eliminate the deviation from the difference spacing when extracting the features of radiomics. Furthermore, before inputting the third module, in addition to resampling all the images, the organ position and range markers and the tumor position and range markers to the same spacing (1 mm, 1 mm, 5 mm), the following steps can be included: use a square subarea with a stride of 5 pixels and a size of 20×20 pixels to capture the image to obtain a plurality of image blocks; delete the image blocks with the organ position and range markers and the tumor position and range markers occupying less than 5% of the total area of the image blocks; and mark the image blocks containing any cancerous parts as cancer blocks, otherwise mark the image blocks containing any non-cancerous parts as non-cancer blocks. Afterwards, all the image blocks are subjected to the 2D feature extraction, analysis and training so as to obtain the third model. The images are captured to obtain a plurality of image blocks, which are trained to obtain the third model, and the third model is able to check the local conditions of the organ.

Figure 2:
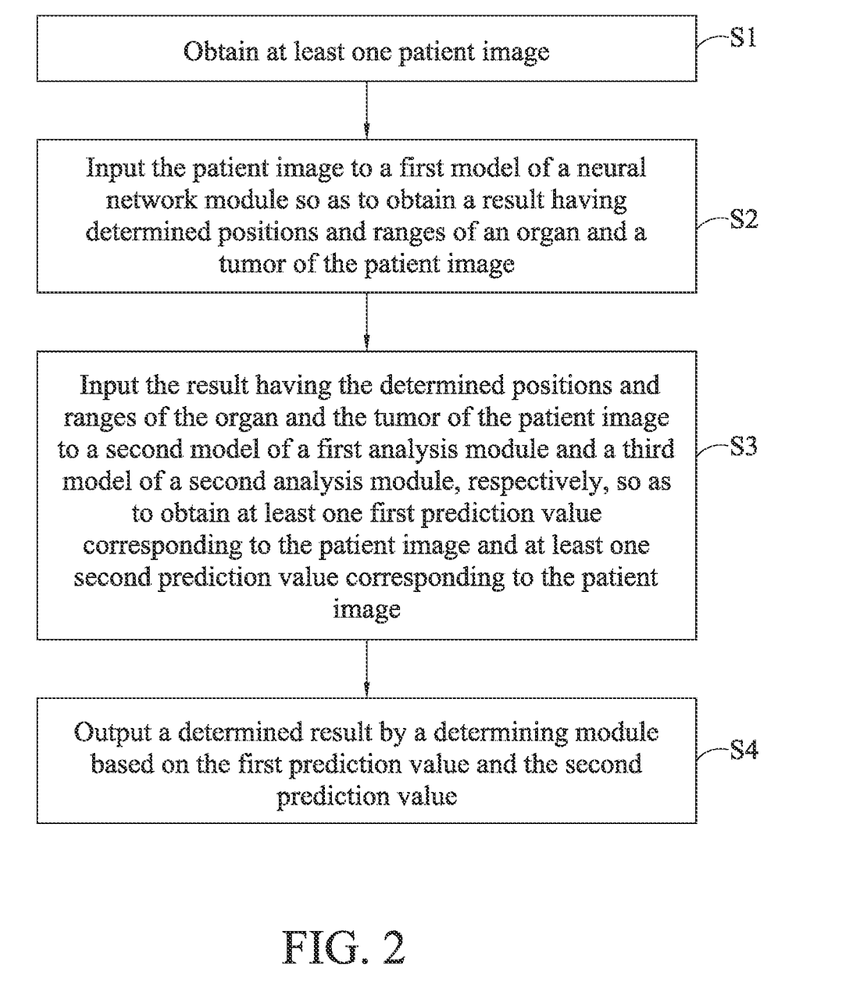
FIG. 2 is a flowchart illustrating a medical image analyzing method according to the present disclosure.

Referring to FIG. 2, a medical image analyzing method according to the present disclosure is further provided. The medical image analyzing method according to the present disclosure can be used in the medical image analyzing system 1. The same technical content between the medical image analyzing method according to the present disclosure and the medical image analyzing system will not be repeated herein.

In step S1, at least one patient image is obtained first. In step S2, the patient image is inputted to a first model of a neural network module 11 so as to obtain a result having determined positions and ranges of an organ and a tumor of the patient image. In step S3, the result having the determined positions and ranges of the organ and the tumor of the patient image is respectively inputted to a second model of a first analysis module 12 and a third model of a second analysis module 13 so as to obtain at least one first prediction value corresponding to the patient image and at least one second prediction value corresponding to the patient image. In step S4, a determining module 14 outputs a determined result based on the first prediction value and the second prediction value. The training methods of the first model, the second model and the third model are the same as the training methods of the first model, the second model and the third model in the medical image analyzing system and will not be repeated herein.

In an embodiment, step S3 further includes the following steps: the threshold-value selection module 16 plots a curve for the first prediction value or the second prediction value, so a threshold value for determining whether there is cancer can be determined from the curve, so that the first analysis module 12 or the second analysis module 13 can determine whether the first prediction value or the second prediction value represents having cancer based on the threshold value.

In an embodiment, in step S4, the determining module 14 can use one of the first prediction value and the second prediction value representing having cancer as a determined result, or use both of the first prediction value and the second prediction value representing having cancer as a determined result, or train based on the first prediction value and the second prediction value to obtain a logistic regression model such that an outcome probability of the logistic regression model is used as the determined result.

In an embodiment, the following step can be performed after step S1 and before step S2, or after step S2 and before step S3: the image preprocessing module 15 processes the image (or patient image) by resampling, windowing and normalization.

The efficacy of the medical image analyzing system and method according to the present disclosure is verified as follows: first, 827 pancreatic cancer patients and 845 pancreatic health computer tomography images are provided; the first model, the second model and the third model are generated by training; the first prediction value and the second prediction value generated by the second model and the third model are combined into the final prediction value by logistic regression method; finally, a sensitivity of 93.4% (95% confidence interval, 87.9%-97.0%) and a specificity of 71.6% (95% confidence interval, 64.5%-78.0%) are obtained, and an area under the curve (AUC) is 0.942 (95% confidence interval, 0.916-0.967); and when the tumor size is less than 2 cm, a sensitivity of 87.2% (95% confidence interval, 72.6%-95.7%) is obtained.

In summary, the medical image analyzing system and method according to the present disclosure have higher sensitivity than radiologists in identifying pancreatic cancer, which means that the medical image analyzing system and method according to the present disclosure can effectively assist radiologists in reducing their clinical missed diagnosis rate, especially in the case of tumors less than 2 cm in size. Therefore, the situation that about 40% of the tumors cannot be detected when the tumor is less than 2 cm in size in the general clinical situation can be effectively improved. In addition, the medical image analyzing system and method according to the present disclosure are automated processes. After directly inputting the original medical image, the medical image analyzing system and method according to the present disclosure can automatically identify the possible positions and ranges of pancreas and tumor and automatically classify whether the original medical image contains pancreatic cancer, so that the present disclosure can be easy to use.

The above-described descriptions of the detailed embodiments are to illustrate the implementation according to the present disclosure, and it is not to limit the scope of the present disclosure. Accordingly, all modifications and variations completed by those with ordinary skill in the art should fall within the scope of present disclosure defined by the appended claims.

What is claimed is:

1. A medical image analyzing system, comprising:
    a neural network module having a first model and configured to input at least one patient image into the first model to obtain a result of determined positions and ranges of an organ and a tumor of the patient image;
    a first analysis module having a second model and configured to input the result of the determined positions and ranges of the organ and the tumor of the patient image into the second model to obtain at least one first prediction value corresponding to the patient image;
    a second analysis module having a third model and configured to input the result of the determined positions and ranges of the organ and the tumor of the patient image into the third model to obtain at least one second prediction value corresponding to the patient image;
    a database stored with a plurality of images, organ position and range markers and tumor position and range markers, wherein the plurality of images, the organ position and range markers and the tumor position and range markers are interlinked to use as a first training set; and
    a determining module configured to output a determined result based on the first prediction value and the second prediction value,
    wherein the neural network module is trained to obtain the first model based on the first training set, wherein the neural network module is a model searched by using a coarse-to-fine neural Architecture search (C2FNAS), and wherein the neural network module uses an Adam optimizer and a cosine annealing learning rate scheduler to adjust a learning rate in a range of $10^{-3}$ to $10^{-5}$, and a loss function is set to a Dice loss combined with a categorical cross-entropy loss.

2. The medical image analyzing system of claim 1, wherein the neural network module obtains a result having determined positions and ranges of the organ and the tumor of the plurality of images by inputting the plurality of images into the first model and uses the result as a second training set.

3. The medical image analyzing system of claim 2, wherein the first analysis module first performs 3D feature analysis on the second training set using an algorithm of radiomics to obtain a plurality of 3D feature values, and then trains a machine learning algorithm of a gradient boosting decision tree using the plurality of 3D feature values to obtain the second model.

4. The medical image analyzing system of claim 3, wherein the first analysis module uses a plurality of filters to extract 3D features, and wherein the plurality of filters include 3 Laplacian of Gaussian filters, 8 wavelet transformation filters and 1 gradient filter.

5. The medical image analyzing system of claim 3, wherein features selected by the radiomics include first order features, gray level co-occurrence matrix features, gray level dependence matrix features, gray level run length matrix features, gray level size zone matrix features, or neighboring gray tone difference matrix features.

6. The medical image analyzing system of claim 2, wherein the second analysis module first performs 2D feature analysis on the second training set using the algorithm of radiomics to obtain a plurality of 2D feature values, and then trains a machine learning algorithm of a gradient boosting decision tree using the plurality of 2D feature values to obtain the third model.

7. The medical image analyzing system of claim 6, wherein the second analysis module uses a plurality of filters to extract 2D features, and wherein the plurality of filters include 4 wavelet transformation filters and 1 gradient filter.

8. The medical image analyzing system of claim 6, wherein features selected by the radiomics include first order features, gray level co-occurrence matrix features, gray level dependence matrix features, gray level run length matrix features, gray level size zone matrix features, or neighboring gray tone difference matrix features.

9. The medical image analyzing system of claim 1, further comprising a threshold-value selection module configured to plot a curve for the first prediction value or the second prediction value, wherein a threshold value for determining whether there is cancer is determined from the curve, such that the first analysis module or the second analysis module determines whether the first prediction value or the second prediction value represents having cancer based on the threshold value.

10. The medical image analyzing system of claim 9, wherein the curve is a receiver operating characteristic curve, and wherein the threshold value is a corresponding threshold value corresponding to a maximum value of a Youden index.

11. The medical image analyzing system of claim 10, wherein the Youden index is calculated from a sensitivity and a specificity corresponding to each point in the curve according to a formula Youden index=sensitivity+specificity−1.

12. The medical image analyzing system of claim 1, wherein the determining module uses an outcome probability of a logistic regression model as the determined result, and wherein the logistic regression model is obtained based on the first prediction value and the second prediction value.

13. The medical image analyzing system of claim 1, wherein the determining module uses one or both of the first prediction value and the second prediction value representing having cancer as the determined result.

14. The medical image analyzing system of claim 1, further comprising an image preprocessing module configured to process the patient image by resampling, windowing and normalization before inputting into the first model, the second model, or the third model.

15. A medical image analyzing method, comprising:
obtaining at least one patient image, and interlinking a plurality of images, organ position and range markers and tumor position and range markers to use as a first training set via a database stored with the plurality of images, the organ position and range markers and the tumor position and range markers;
inputting the patient image into a first model of a neural network module to obtain a result having determined positions and ranges of an organ and a tumor of the patient image, wherein the neural network module is trained to obtain the first model based on the first training set, wherein the neural network module is a model searched by using a coarse-to-fine neural Architecture search (C2FNAS), and wherein the neural network module uses an Adam optimizer and a cosine annealing learning rate scheduler to adjust a learning rate in a range of $10^{-3}$ to $10^{-5}$, and a loss function is set to a Dice loss combined with a categorical cross-entropy loss;
inputting the result having determined positions and ranges of the organ and the tumor of the patient image into a second model of a first analysis module and a third model of a second analysis module, respectively, to obtain at least one first prediction value corresponding to the patient image and at least one second prediction value corresponding to the patient image; and
outputting a determined result by a determining module according to the first prediction value and the second prediction value.

16. The medical image analyzing method of claim 15, wherein the neural network module obtains a result having determined positions and ranges of the organ and the tumor of the plurality of images by inputting the plurality of images into the first model and uses the result as a second training set.

17. The medical image analyzing method of claim 16, wherein the first analysis module first performs 3D feature analysis on the second training set using an algorithm of radiomics to obtain a plurality of 3D feature values, and then trains a machine learning algorithm of a gradient boosting decision tree using the plurality of 3D feature values to obtain the second model.

18. The medical image analyzing method of claim 17, wherein the first analysis module uses a plurality of filters to extract 3D features, and wherein the plurality of filters include 3 Laplacian of Gaussian filters, 8 wavelet transformation filters and 1 gradient filter.

19. The medical image analyzing method of claim 17, wherein features selected by the radiomics include first order features, gray level co-occurrence matrix features, gray level dependence matrix features, gray level run length matrix features, gray level size zone matrix features, or neighboring gray tone difference matrix features.

20. The medical image analyzing method of claim 16, wherein the second analysis module first performs 2D feature analysis on the second training set using the algorithm of radiomics to obtain a plurality of 2D feature values, and then trains a machine learning algorithm of a gradient boosting decision tree using the plurality of 2D feature values to obtain the third model.

21. The medical image analyzing method of claim 20, wherein the second analysis module uses a plurality of filters to extract 2D features, and wherein the plurality of filters include 4 wavelet transformation filters and 1 gradient filter.

22. The medical image analyzing method of claim 20, wherein features selected by the radiomics include first order features, gray level co-occurrence matrix features, gray level dependence matrix features, gray level run length matrix features, gray level size zone matrix features, or neighboring gray tone difference matrix features.

23. The medical image analyzing method of claim 15, further comprising plotting a curve for the first prediction value or the second prediction value by a threshold-value selection module, wherein a threshold value for determining whether there is cancer is determined from the curve, such that the first analysis module or the second analysis module determines whether the first prediction value or the second prediction value represents having cancer based on the threshold value.

24. The medical image analyzing method of claim 23, wherein the curve is a receiver operating characteristic curve, and wherein the threshold value is a corresponding threshold value corresponding to a maximum value of a Youden index.

25. The medical image analyzing method of claim 24, wherein the Youden index is calculated from a sensitivity and a specificity corresponding to each point in the curve according to a formula Youden index=sensitivity+specificity−1.

26. The medical image analyzing method of claim 15, wherein the determining module uses an outcome probability of a logistic regression model as the determined result, and wherein the logistic regression model is obtained based on the first prediction value and the second prediction value.

27. The medical image analyzing method of claim 15, wherein the determining module uses one or both of the first prediction value and the second prediction value representing having cancer as the determined result.

28. The medical image analyzing method of claim 15, further comprising enabling an image preprocessing module to process the patient image by resampling, windowing and normalization before inputting into the first model, the second model, or the third model.

\* \* \* \* \*